(12) United States Patent
Simon et al.

(10) Patent No.: US 10,172,965 B2
(45) Date of Patent: Jan. 8, 2019

(54) HIGH PURITY THERAPEUTIC BONE AGENTS

(71) Applicant: IsoTherapeutics Group, LLC, Angleton, TX (US)

(72) Inventors: Jaime Simon, Angleton, TX (US); R. Keith Frank, Lake Jackson, TX (US); David A. Wilson, Lake Jackson, TX (US)

(73) Assignee: IGL Pharma, Inc., Angleton, TX (US)

( * ) Notice: Subject to any disclaimer, the term of this patent is extended or adjusted under 35 U.S.C. 154(b) by 43 days.

(21) Appl. No.: 15/027,280

(22) PCT Filed: Oct. 7, 2014

(86) PCT No.: PCT/US2014/059385
§ 371 (c)(1),
(2) Date: Apr. 5, 2016

(87) PCT Pub. No.: WO2015/054173
PCT Pub. Date: Apr. 16, 2015

(65) Prior Publication Data
US 2016/0250359 A1    Sep. 1, 2016

Related U.S. Application Data

(60) Provisional application No. 61/887,603, filed on Oct. 7, 2013.

(51) Int. Cl.
*A61K 51/04* (2006.01)
*A61K 51/12* (2006.01)
*G21G 1/02* (2006.01)
*G21G 1/00* (2006.01)

(52) U.S. Cl.
CPC .......... *A61K 51/0482* (2013.01); *G21G 1/02* (2013.01); *G21G 2001/0094* (2013.01)

(58) Field of Classification Search
CPC ......... A61K 51/00; A61K 51/04; A61K 51/12
See application file for complete search history.

(56) References Cited

U.S. PATENT DOCUMENTS

| | | | |
|---|---|---|---|
| 4,882,142 A | * | 11/1989 | Simon ............... A61K 51/0482 424/1.77 |
| 7,928,113 B2 | | 4/2011 | Neamati et al. |
| 2004/0258614 A1 | | 12/2004 | Line et al. |
| 2006/0233797 A1 | | 10/2006 | Gujrathi |
| 2009/0041740 A1 | | 2/2009 | Pownall et al. |

FOREIGN PATENT DOCUMENTS

EP    0462787 B1    6/1995

OTHER PUBLICATIONS

Samarium (https://en.wikipedia.org/wiki/Samarium; downloaded on Aug. 15, 2017).*
Ali Bahrami-Samani et al. Production, Quality Control and Biological Evaluation of 153-Sm-EDTMP in Wild-Type Rodents, Iran J Nucl. Med, 17(2), 12-19. (Year: 2009).*

* cited by examiner

*Primary Examiner* — Michael G. Hartley
*Assistant Examiner* — Jagadishwar R Samala
(74) *Attorney, Agent, or Firm* — Technology Law, PLLC; Karen L. Kimble

(57) ABSTRACT

This invention relates to radioactive, bone-seeking, pharmaceutical methods, compositions and formulations that have a lower impurity profile, a longer shelf life, improved availability and are less expensive to prepare. The compositions of this invention can be conveniently prepared in a timely manner resulting in improved availability and delivery of the drugs to patients.

2 Claims, No Drawings

HIGH PURITY THERAPEUTIC BONE AGENTS

BACKGROUND OF THE INVENTION

Field of the Invention

This invention relates to bone-seeking radioactive metal-chelant compositions that are suitable for administration to a Patient having: bone pain; one or more calcific tumors; or in need of a bone marrow suppression procedure.

Description of Related Art

Radiopharmaceuticals based on metal-chelant complexes have been used to diagnose and treat bone cancer. For example, Quadramet® (trademark of Lantheus Medical Imaging, Inc.) is a commercially available chelate formed between Sm-153 and ethylene-diaminetetramethylenephosphonic acid (EDTMP) that is currently indicated for the pain associated with bone metastases (U.S. Pat. No. 4,898,724). Typical dosages are 1 mCi of Sm-153 per kg body weight of the patient. Thus for a 70 kg patient the dosage would be 70 mCi.

U.S. Pat. No. 5,059,412 teaches the use of Sm-153, Gd-159, Ho-166, Lu-177 and Yb-175 chelates with chelants derived from the 1,4,7,10-tetraazacyclododecane moiety including 1,4,7,10-tetraazacyclododecanetetramethylenephosphonic acid (DOTMP), while U.S. Pat. No. 5,064,633 teaches the above metals plus Y-90. Compositions of Sm, Gd, Ho, Lu and Y with DOTMP comprising predominately non-radioactive metal with the corresponding radioactive metal (e.g. Sm-152 with Sm-153 at µCi levels) were prepared and biodistribution data in rats was obtained.

A therapeutically effective biodistribution (fate of the activity after administration) for a therapeutic bone agent includes high bone uptake, low soft tissue uptake, rapid clearance of the activity not associated with bone, and high lesion-to-normal bone ratio. Compositions that do not have these characteristics are detrimental to the patient. For example, high soft tissue uptake would result in the patient receiving a high radiation dose to the liver, bone marrow or other soft tissue leading to undesirable side effects.

Radionuclides such as Sm-153 are prepared in a nuclear reactor by bombarding purified targets of the element containing one less neutron and in the process generate radionuclidic impurities. For example, to produce Sm-153 the target that is irradiated is Sm-152. When Sm-153 decays, Eu-153 is formed and an unwanted impurity, radioactive Eu-154 is formed from neutron capture by Eu-153.

The impurities can be detrimental to institutions from both a patient and a waste disposal standpoint. For example, too much Eu-154 administered to a patient would result in the isotope giving an undesirable dose to a patient for a long period of time because of its half-life of 8.8 years. In addition, the dose that is excreted in the urine by the patient containing Eu-154 is a concern and institutions may be forced to collect the radioactive urine. Disposal of the product vials containing residual activity can be a problem. These vials and syringes are typically allowed to decay for 10 half-lives prior to disposal. This is a reasonable amount of time for Sm-153 (about 20 days) but not for Eu-154 (about 88 years). Processes must be implemented in order to deal with waste disposal of vials and syringes that are used. This makes the use of these types of radiopharmaceuticals more complex and institutions may chose not to use the drugs.

In addition, these long-lived impurities cause issues with the radioactive licensing process for the institution. Typically institutions are only allowed small amounts of long-lived radionuclides (having half-lives greater than 120 days) before they are required to have financial assurance. Financial assurance can be very expensive especially for institutions that only handle short-lived isotopes.

The specifications for Quadramet® call for the product to contain less than 0.093 microcuries (µCi) of Eu-154 per millicurie (mCi) of Sm-153 at Expiration Date (http://health.phys.iit.edu/extended_archive/0001/msg00922.html, http://acnp-cal .org/SM1531NS.html) or 4 days from the manufacture date (http://www.ibamolecular.eu/products/quadrainet). This restriction limits the expiration time of the drug. Since Sm-153 decays faster than Eu-154, the longer the Sm-153 solution decays, the higher the amount of Eu-154 in the sample relative to Sm-153. Thus expiration of not only formulated Quadramet® (e.g. Ca-EDTMP + Sm-153) but also the Sm-153 used to produce Quadramet® is limited by the amount of Eu-154 in the sample.

In nuclear reactors such as the one at the University of Missouri in Columbia, Mo., the Sm-152 samples are irradiated for one week in the "flux trap" in order to produce the high specific activity Sm-153 required for the production of Quadramet®. The flux trap is only accessed once a week and therefore high specific activity Sm-153 can only be produced on a weekly basis. Because of the growing amount of Eu-154 compared to Sm-153, the isotope can only be used for a short period of time. Thus the drug is not available to treat patients on some days of the week. The flux trap portion of the reactor is also the most expensive to access (requiring reactor shut-down), thus increasing the production cost of the isotope.

Clearly, there is a need for a product with a longer shelf life and a better impurity profile.

BRIEF SUMMARY OF THE INVENTION

The present invention provides a method for the treatment of a Patient comprising administration to the Patient having bone pain, one or more calcific tumors, or in need of a bone marrow suppressing procedure, a pharmaceutically-acceptable formulation of a chelate composition comprising a Clinically Relevant Dosage of the composition that is therapeutically effective, said composition possessing an extended Expiration Date of greater than or equal to about 5 days and said chelate comprises Sm-153 and DOTMP or a physiologically-acceptable salt thereof wherein the Sm-153 dosage is at least 35 mCi.

The formulation of this invention comprises a chelate composition either as a pre-mixed drug ready for use or a kit having two separate components, the chelant and the isotope, which components are mixed to form the chelate composition at the appropriate time prior to use in the method.

Also provided is the chelate composition comprising a Clinically Relevant Dosage of the composition that is therapeutically effective and pharmaceutically-acceptable, said composition possessing an extended Expiration Date of greater than or equal to about 5 days and said chelate comprises Sm-153 and DOTMP or a physiologically-acceptable salt thereof wherein the Sm-153 dosage is at least 35 mCi.

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

% means weight percent, unless stated otherwise

Clinically Relevant Dosage means enough activity to cause either pain palliation or reduction of tumor burden. This dosage is about 0.5 mCi per kg body weight or about 35 mCi for a 70 kg patient; more preferred 1.0 mCi per kg body weight or about 70 mCi for a 70 kg patient. Higher amounts of radioactivity may be administered to the patients or for treating tumor regression or bone marrow ablation in patients.

DOTMP means 1,4,7,10-tetraazacyclododecanetetramethylenephosphonic acid

EDTMP means ethylenediaminetetramethylenephosphonic acid

Expiration Date means the number of days after production when a Sm-153 bone agent formulation contains equal to or greater than 0.093 microcuries of Eu-154 per mCi of Sm-153.

FDA means US Food and Drug Administration including its regulations

Patient means an animal or human in need of treatment

Ci means curies

µCi means microcuries mCi means millicuries

Discussion

The specific activity of an isotope is sometimes a source of confusion because it is expressed in many ways (see Practical Aspects of labeling DTPA and DOTA peptides with Y-90, In-111, Lu-177 and Ga-68 for Peptide-Receptor Scintigraphy and peptide-Receptor Radionuclide Therapy in preclinical and Clinical Applications (http://pharmacyce.unm.edu/program_information/freelessonfiles/Vol16Lesson5.pdf).

For this invention, the specific activity of an isotope is defined as the radioactivity of the isotope in question divided by the mass of all of the isotopes (stable and radioactive) of that element. For example for reactor produced Sm-153 where the starting material is Sm-152 that is converted to Sm-153, the specific activity of Sm-153 is the amount of radioactivity of Sm-153 in the sample divided by the total mass of Sm in the sample (e.g. activity Sm-153/sum of masses of Sm-152 and Sm-153). The units of the number are typically in Curies per gram (Ci/g) or milliCuries per milligram (mCi/mg). In some cases the percent of the isotope that is radioactive is reported. For example in reactor produced Sm-153, only about 2% of the Sm is Sm-153 and about 98% is non-radioactive Sm-152.

Traditionally, nuclear medicine scientists strive to increase the specific activity of the isotopes of interest. For example, two government grants for providing high specific activity isotopes have been recently granted (High Specific Activity Sm-153 by Post Irradiation Isotope Separation, DOE SBIR grant Solicitation Number DE-FOA-0000676, Production of Commercial High Specific Activity Sn-117m Radiochemical and Chelates, DOE grant Solicitation Number DE-FOA-000782). The use of high specific activity isotopes allows for less mass of the element needed to achieve the same amount of radioactivity. This leads to lower amounts of chelating agents and/or proteins needed in the radioactive drug. In addition, in many cases such as with labeled antibodies and proteins, the receptors on cells (such as cancer cells) that the drugs target are limited. If the specific activity of the isotope is low (e.g. 2% of the atoms are radioactive), then the amount of active drug that reaches the target is relatively small. However, if the specific activity is high (e.g. 100% of the atoms are radioactive), then the amount of effective drug that reaches the target is much higher, which explains why so much effort is put forth in radioisotope production to achieve higher and higher specific activity.

Contrary to this conventional wisdom where higher specific activity isotopes are sought-after as desirable, this invention utilizes Sm-153 produced in a lower flux portion of the nuclear reactor for a shorter period of time, resulting in a lower specific activity isotope with a significant cost reduction and lower impurity profile. When combined with DOTMP a product can be produced which comprises a Clinically Relevant Dosage of Sm-153-DOTMP with a reduced radionuclidic impurity profile, a longer shelf life, a lower cost to manufacture, and can be made available to patients on a more frequent basis.

The formulations of the present invention may be in a kit form such that the two components (chelant and isotope) are mixed at the appropriate time prior to use or provided pre-mixed as the ready to use drug. Whether pre-mixed as the drug or as a kit where the drug is made on site, the formulations require a pharmaceutically-acceptable carrier. Such carriers comprise any suitable pharmaceutically-acceptable carrier such as one or more of a suitable solvent, preservatives, diluents, excipients and buffers. Useful solvents include, for example, water, aqueous alcohols and glycols. The formulation is administered to the Patient by injection intravenously or intramuscularly.

The invention will be further clarified by a consideration of the following examples, which are intended to be purely exemplary of the invention.

Materials and Equipment

The radioactive isotopes were purchased from The University of Missouri Research Reactor.

Chelants were purchased from commercial sources or were prepared as described in U.S. Pat. No. 5,059,412.

General Procedure

In the following examples, the lettered examples are comparative, and the numbered examples are this invention.

EXAMPLE A

Comparative

A Quadramet® formulation containing 105 mg of EDTMP and 150 mCi of Sm-153 was prepared. This quantity is normally enough to treat 2 patients weighing 70 kg at a 1 mCi/kg dosage. Sm-153 is prepared by irradiating Sm-152 in a nuclear reactor for 155 hours with a thermal neutron flux of $2.20 \times 10^{14}$ neutrons/cm$^2$-sec. The specific activity of the Sm-153 is 6,650 mCi/mg at end of irradiation and contains 0.0181 µCi of Eu-154 per mCi of Sm-153.

After 5 days of radioactive decay however, the specific activity of the Sm-153 is 1,102 mCi/mg but the activity of the Eu-154 impurity is 0.1092 µCi Eu-154 per mCi of Sm-153. This exceeds the FDA allowable amount of Eu-154 (0.093 µCi of Eu-154 per mCi of Sm-153) by 17%. A Quadramet formulation prepared by combining 150 mCi of this decayed Sm-153 with EDTMP contains 16.38 µCi of Eu-154 (0.1092 µCi of Eu-154 per mCi Sm-153) and is thus out of spec and can no longer be used.

EXAMPLE B

Comparative

Sm-153 is prepared by irradiating Sm-152 in a nuclear reactor for 48 hours with a thermal neutron flux of $8.00 \times 10^{13}$ neutrons/cm$^2$-sec. The specific activity of the Sm-153 is 1,430 mCi/mg at end of irradiation and contains 0.0005 µCi of Eu-154 per mCi of Sm-153. After 5 days of radioactive decay, the specific activity of the Sm-153 is 237 mCi/mg and the the activity of the Eu-154 impurity is 0.00296 µCi of Eu-154 per mCi of Sm-153. This is below the FDA allowable amount of Eu-154 (0.093 µCi of Eu-154 per mCi of Sm-153). However, the Quadramet® formulation requires a minimum EDTMP to Sm mole ratio of 273:1 in order to properly control the biodistribution of Sm-153 (calculated from the data in Quadramet® package insert). Because of this requirement the maximum mass of Sm used in a Quadramet preparation is about 0.134 mg. Therefore at a specific activity of 237 mCi/mg only about 32 mCi can be prepared. This is not a sufficient dosage to treat a 70 kg patient at 1 mCi/kg or even a 70 kg patient at 0.5 mCi/kg.

EXAMPLE 1

Sm-153 is prepared by irradiating Sm-152 in a nuclear reactor for 48 hours with a thermal neutron flux of $8.00 \times 10^{13}$ neutrons/cm$^2$-sec. The specific activity of the Sm-153 is 1,430 mCi/mg at end of irradiation and contains 0.0005 µCi of Eu-154 per mCi of Sm-153. After 5 days the specific activity is 0.237 Ci/mg and the activity of the impurity Eu-154 is 0.00296 µCi Eu-154 per mCi of Sm-153. This is 3.2% of the FDA allowable maximum amount of Eu-154. Since Sm-153-DOTMP can be prepared using a 1:1 mole ratio of DOTMP to Sm, a preparation using 10 mg of DOTMP and 657 mCi (2.77 mg Sm) of the 5 day old Sm-153 is made. This composition produces sufficient quantities of Sm-153 to treat 9 patients weighing an average of 70 kg at 1 mCi/kg and has an Expiration Date of greater than 5 days.

EXAMPLE 2

A formulation, prepared as in Example 1, is allowed to decay 10 days. The amount of Sm-153 in the formulation is now 110 mCi which is sufficient to treat one patient with a weight of 70 kg at 1 mCi of Sm-153 per kg body weight. The formulation contains 0.0178 µCi of Eu-154 per mCi of Sm-153 which is 19% of the allowable amount of Eu-154. Therefore, the composition has a greater than 10 day Expiration Date.

EXAMPLE 3

A formulation, prepared as in Example 1, is allowed to decay 13 days. The amount of Sm-153 in the formulation is now 37 mCi which is sufficient to treat one patient with a weight of 70 kg at 0.5 mCi of Sm-153 per kg body weight. The formulation contains 0.05228 µCi of Eu-154 per mCi of Sm-153 which is 56% of the allowable amount of Eu-154. Therefore, the formulation has a greater than 13 day Expiration Date.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A process for preparing a pharmaceutically-acceptable formulation of a radioactive chelate composition comprising the steps of:
    a) irradiating Sm-152 in a lower flux portion of the nuclear reactor having less than $8.5 \times 10^{13}$ neutron/cm$^2$-sec to form low specific activity Sm-153, wherein the isotope composition after the irradiation contains mainly Sm-152 and Sm-153 with impurity of Eu-154 less than 0.093,µCi Eu-154/ mCi Sm-153 after 5 days of decay, thereby providing an extended Expiration Date greater than or equal to about 5 days;
    b) taking the prepared isotope mixture from step a) and either using it in step c) or allowing it to decay and then using it in step c) which decay further lowers the specific activity of the Sm-153 formed in step a) while maintaining less than 0.093 µCi of Eu-154 per mCi of Sm-153; and
    c) reacting DOTMP or a physiologically-acceptable salt thereof as the chelant with the Sm-153 isotope mixture from step b) in an, aqueous solvent to form the radioactive chelate composition wherein the Sm-153 dosage is at least 35 mCi that is pharmaceutically-acceptable and has a Clinically Relevant Dosage that is therapeutically effective.

2. The process of claim 1 wherein the Sm-153 isotope of step (b) and step (c) is used without further dilution with non-radioactive Sm.

* * * * *